United States Patent [19]

Hayata et al.

[11] Patent Number: 5,080,990
[45] Date of Patent: Jan. 14, 1992

[54] ELECTROPHOTOGRAPHIC PHOTORECEPTOR HAVING CHARGE TRANSPORT MATERIAL

[75] Inventors: Hirofumi Hayata; Shinichi Suzuki; Osamu Sasaki, all of Tokyo, Japan

[73] Assignee: Konica Corporation, Tokyo, Japan

[21] Appl. No.: 569,944

[22] Filed: Aug. 20, 1990

[30] Foreign Application Priority Data

Aug. 22, 1989 [JP] Japan ............................ 1-217078

[51] Int. Cl.$^5$ ............................................. G03G 5/14
[52] U.S. Cl. .................................................... 430/59
[58] Field of Search ........................................ 430/59

[56] References Cited

U.S. PATENT DOCUMENTS 4,495,261 1/1985 Takahashi ........................ 430/58
4,725,518 2/1988 Carmichael ..................... 430/59 X

*Primary Examiner*—David Welsh
*Attorney, Agent, or Firm*—Finnegan, Henderson, Farabow, Garrett, and Dunner

[57] ABSTRACT

An electrophotographic photoreceptor is disclosed, which comprises a conductive support and a photosensitive layer containing a compound represented by the following Formula I as a carrier-transporting substance:

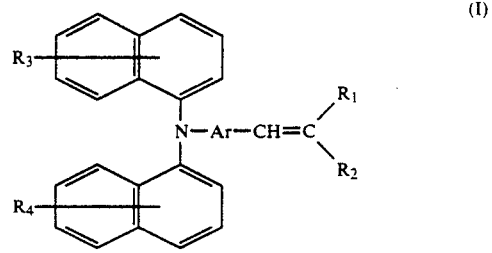

(I)

wherein Ar is a substituted or unsubstituted arylene group; $R_1$ and $R_2$ are each a hydrogen atom, a substituted or unsubstituted alkyl group having 1 to 5 carbon atoms or a substituted or unsubstituted aryl group; $R_3$ and $R_4$ are each a hydrogen atom, a hydroxyl group, a substituted or unsubstituted alkoxy group having 1 to 5 carbon atoms or a substituted or unsubstituted alkyl group having 1 to 5 carbon atoms.

The photoreceptor is excellent in charge characteristics, light sensitivity and image formation and less causes fatigue deterioration after repeated use, thus having a superior durability.

3 Claims, 1 Drawing Sheet

ELECTROPHOTOGRAPHIC PHOTORECEPTOR HAVING CHARGE TRANSPORT MATERIAL

FIELD OF THE INVENTION

The present invention relates to an electrophotographic photoreceptor. More particularly, it relates to an electrophotographic photoreceptor comprising a photosensitive layer containing a carrier-generating material and a carrier-transporting material.

BACKGROUND OF THE INVENTION

Electrophotographic photoreceptors have been hitherto known to include those comprising a photosensitive layer containing as a main component an inorganic photosensitive material such as selenium, zinc oxide, cadmium sulfide or silicon. These, however, can not necessarily be satisfactory in view of characteristics such as thermal stability and durability, and also have certain problems in the manufacture and handling.

On the other hand, electrophotographic photoreceptors comprising a photosensitive layer mainly composed of an organic photoconductive compound have a number of advantages that they can be manufactured relatively with ease, are inexpensive, can be handled with ease, and also commonly have superior thermal stability compared with a selenium photoreceptor. Poly-N-vinylcarbazole is most well known as the organic photoconductive compound, and a photoreceptor comprising a photosensitive layer mainly composed of a charge-moving complex formed of this poly-N-vinylcarbazole and a Lewis acid such as 2,4,7-trinitro-9-fluolenone has been already put into practical use.

Also known is a photoreceptor comprising a function-separated photosensitive layer of a laminated layer type or single layer type in which the function of carrier generation and the function of carrier transport are allotted respectively to different materials. For example, a photoreceptor comprising a photosensitive layer comprised of a carrier generation layer comprising an amorphous selenium thin layer and a carrier transport layer containing poly-N-vinylcarbazole as a main component has been already put into practical use.

The poly-N-vinylcarbazole, however, lacks in flexibility, and a coating thereof is so hard and brittle that cracks or peeling tends to occur. Hence, a photoreceptor in which this compound is used has a poor durability, and, even when a plasticizer is added so that this disadvantage can be eliminated, may have a large residual potential at the time of electrophotographic processing. This residual potential is accumulated as a result of repeated use to gradually make fog greater, resulting in a damage of copied images.

A low-molecular organic photoconductive compound usually has no film-forming properties, and hence is used in combination with a suitable binder. This compound is preferable in view of the advantage that the physical properties or photosensitive characteristics of a coating can be controlled to a certain degree by selecting kinds, composition and so forth of the binder. There, however, is a limit in the kinds of an organic photoconductive compound having a high compatibility with the binder. Actually, there are only a little kinds of binder that can be used to constitute a photosensitive layer of a photoreceptor, in particular, an electrophotographic photoreceptor.

For example, 2,5-bis(p-diethylaminophenyl)-1,3,4-oxadiazole, as disclosed in U.S. Pat. No. 3,189,447, has a low compatibility with a binder as exemplified by polyester or polycarbonate commonly used as a material for the photosensitive layer of an electrophotographic photoreceptor. Hence, formation of a photosensitive layer by mixing it in the amount necessary for regulating electrophotographic characteristics may result in deposition of oxadiazole at temperatures higher than 50° C., bringing about the disadvantage that the electrophotographic characteristics such as charge retention and sensitivity may be lowered.

On the other hand, a diarylalkane derivative, as disclosed in U.S. Pat. No. 3,820,989, has less problem of the compatibility with binders, but has a small stability to light. Hence, it has the disadvantage that use thereof in a photosensitive layer of a photoreceptor used in repetitive transfer electrophotography in which the photosensitive layer is repeatedly charged and exposed to light may result in a gradual lowering of the sensitivity of the photosensitive layer.

U.S. Pat. No. 3,274,400 and Japanese Patent Examined Publication No. 36428/1972 disclose phenothiazine derivatives of respectively different types. Both of these, however, are disadvantageous in that they have a low sensitivity and also have a low stability in repeated use.

Stilbene compounds as disclosed in Japanese Patent Publications Open to Public Inspection (hereinafter referred to as Japanese Patent O.P.I. Publication) No. 65440/1983 and No. 198043/1983 have relatively good charge retention and sensitivity, but are not satisfactory in respect of the durability in repeated use. In addition, these compounds leave an unsettled problem in respect of the sensitivity at a low potential.

Thus, under the existing circumstances, no carrier-transporting material has been discovered which has practically satisfactory characteristics in the manufacture of electrophotographic photoreceptors.

SUMMARY OF THE INVENTION

An object of the present invention is to provide a photoreceptor having a high sensitivity.

Another object of the present invention is to provide an electrophotographic photoreceptor having a high sensitivity and yet a low residual potential.

Still another object of the present invention is to provide an photoreceptor having a high sensitivity even at a low potential.

A further object of the present invention is to provide an electrophotographic photoreceptor having a superior durability, which may undergo less fatigue deterioration caused by repeated use and can retain stable characteristics over a long period of time, when used as a photoreceptor for repetitive transfer electrophotography in which the steps of charging, exposure, development and transfer are repeated.

The above objects of the invention can be achieved by an electrophotographic photoreceptor comprising a conductive support and a layer being provided on the support and containing a compound represented by the following Formula I as a carrier-transporting material. Formula I wherein Ar represents a substituted or unsubstituted arylene group; $R_1$ and $R_2$ each represent a hydrogen atom, a substituted or unsubstituted alkyl group having 1 to 5 carbon atoms, or a substituted or unsubstituted aryl group; $R_3$ and $R_4$ each represent a hydrogen atom, a halogen atom, a hydroxyl group, a substituted or unsubstituted alkoxy group having 1 to 5 carbon atoms, a substituted or unsubstituted alkyl group having 1 to 5 carbon atoms.

DETAILED DESCRIPTION OF THE INVENTION

In the above Formula I, the alkyl group represented by $R_3$ and $R_4$ includes a methyl group, an ethyl group, a propyl group and a butyl group; the alkoxy group includes a methoxy group and an ethoxy group; and the halogen atom includes a fluorine atom, a chlorine atom, a bromine atom, and an iodine atom.

The arylene group represented by Ar includes a phenylene group and a naphthylene group.

The alkyl group represented by $R_1$ and $R_2$ includes a methyl group, an ethyl group, a propyl group and a butyl group; and the aryl group includes a phenyl group and a naphthyl group.

Examples of the compound according to the present invention, represented by Formula I, are shown below.

| No | Ar | $R_1$ | $R_2$ | $R_3$ | $R_4$ |
|---|---|---|---|---|---|
| 1 | ―⌬― | ―H | ―⌬ (phenyl) | H | H |
| 2 | " | " | ―⌬―CH$_3$ | " | " |
| 3 | " | " | ―⌬―OCH$_3$ | " | " |
| 4 | " | " | ―⌬―Cl | " | " |
| 5 | " | " | ―⌬―N(C$_2$H$_5$)$_2$ | " | " |
| 6 | " | " | ―⌬―C$_2$H$_5$ | " | " |
| 7 | " | " | ―⌬(m-CH$_3$) | " | " |
| 8 | " | " | ―⌬(m-Cl) | " | " |

-continued

| No | Ar | $R_1$ | $R_2$ | $R_3$ | $R_4$ |
|---|---|---|---|---|---|
| 9 | " | " |  | " | " |
| 10 | " | " |  | " | " |
| 11 | " | " |  | 4-$CH_3$ | 4'-$CH_3$ |
| 12 | " | " |  | 5-$OCH_3$ | 5'-$OCH_3$ |
| 13 | " | " |  | 8-Cl | 8'-Cl |
| 14 |  |  |  | H | H |
| 15 | " | " |  | " | " |
| 16 | " | " |  | " | " |
| 17 | " | " |  | " | " |
| 18 | " | " |  | " | " |
| 19 | " | " |  | " | " |
| 20 | " | " |  | " | " |

-continued

| No | Ar | R₁ | R₂ | R₃ | R₄ |
|----|----|----|----|----|----|
| 21 | " | " |  3-Cl-phenyl | " | " |
| 22 | " | " |  3-OCH₃-phenyl | " | " |
| 23 | " | " |  3,5-di-CH₃-phenyl | " | " |
| 24 | " | " |  phenyl | 4-CH₃ | 8'-CH₃ |
| 25 | " | " |  phenyl | 4-OCH₃ | H |
| 26 | " | " |  phenyl | 2-Cl | H |
| 27 |  naphthyl | —H |  phenyl | H | H |
| 28 | " | " |  4-CH₃-phenyl | " | " |
| 29 | " | " |  4-OCH₃-phenyl | " | " |
| 30 | " | " |  4-Cl-phenyl | " | " |
| 31 | " | " |  4-N(C₂H₅)₂-phenyl | " | " |
| 32 | " | " |  4-C₂H₅-phenyl | " | " |

-continued

| No | Ar | R₁ | R₂ | R₃ | R₄ |
|----|----|----|----|----|----|
| 33 | " | " |  (3-CH₃-phenyl) | " | " |
| 34 | " | " |  (3-Cl-phenyl) | " | " |
| 35 | " | " |  (3-OCH₃-phenyl) | " | " |
| 36 | " | " |  (3,5-diCH₃-phenyl) | " | " |
| 37 | " | " |  (phenyl) | 6-CH₃ | H |
| 38 | " | " |  (phenyl) | 7-OCH₃ | 7'-OCH₃ |
| 39 | " | " |  (phenyl) | 3-Cl | H |
| 40 |  (1,4-naphthyl) |  (phenyl) |  (phenyl) | H | H |
| 41 | " | " |  (4-CH₃-phenyl) | " | " |
| 42 | " | " |  (4-OCH₃-phenyl) | " | 6' |
| 43 | " | " |  (4-Cl-phenyl) | " | " |

-continued

| No | Ar | R₁ | R₂ | R₃ | R₄ |
|----|----|----|----|----|----|
| 44 | " | " |  | " | " |
| 45 | " | " |  | " | " |
| 46 | " | " |  | " | " |
| 47 | " | " |  | " | " |
| 48 | " | " |  | " | " |
| 49 | " | " |  | " | " |
| 50 | " | " |  | 4-CH₃ | 6'-CH₃ |
| 51 | " | " |  | 8-OCH₃ | 3'-OCH₃ |
| 52 | " | " |  | 6-Cl | 4'-Cl |
| 53 |  |  |  | H | H |
| 54 | " |  |  | " | " |

-continued

| No | Ar | R₁ | R₂ | R₃ | R₄ |
|----|----|----|----|----|----|
| 55 |  | —CH₃ | —CH₃ | " | " |
| 56 |  | —Cl | —Cl | " | " |
| 57 |  CH₃ | —CH₃ | —CH₃ | " | " |
| 58 |  CH₃ |  |  | " | " |

A synthesis example of the compound of the present invention is shown below.

Synthesis of Exemplary Compound 14

In 25 ml of N,N-dimethylformamide, 4.0 g of potassium t-butoxide was dispersed at room temperature and in a nitrogen atmosphere. To the resulting dispersion, a solution obtained by dissolving 1.5 g of N,N-dinaphthyl-4-formylaniline and 1.7 g of diethyl diphenylmethyl phosphonate in 25 ml of N,N-dimethylformamide was dropwise added. Thereafter, the mixture was stirred at room temperature for 1 hour. The resulting reaction mixture was poured in 500 ml of water, and extracted with 200 ml of toluene. Then organic layer was washed with water, and, after removal of the solvent, recrystallized with toluene-hexane to give 2.8 g of an end product (yield: 90%). m.p.: 181° to 182° C.

Various forms are known as the structure of electrophotographic photoreceptors. Any form of them may be taken in the electrophotographic photoreceptor of the present invention.

In usual instances, the forms as shown in FIGS. 1 to 6 are taken. In the photoreceptor shown in FIGS. 1 or 2, it comprises a conductive support 1 and provided thereon a photosensitive layer 4 comprising a laminated structure formed of a carrier generation layer 2 mainly composed of a carrier-generating material and a carrier transport layer 3 mainly composed of a carrier-transporting material.

Figure 1:
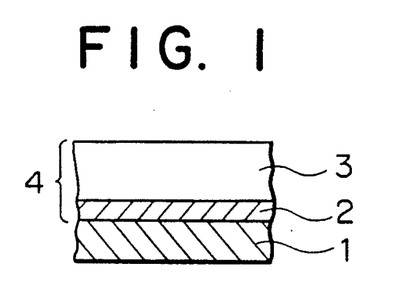
FIGS. 1 to 6 schematically illustrates cross sections of examples of the photoreceptor of the present invention.
Figure 2:
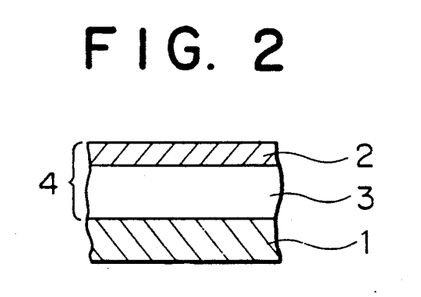
Figure 3:
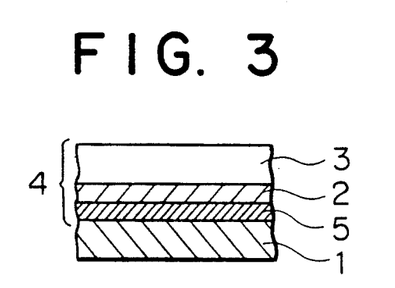
Figure 4:
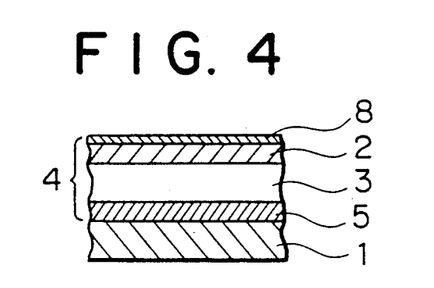
Figure 5:
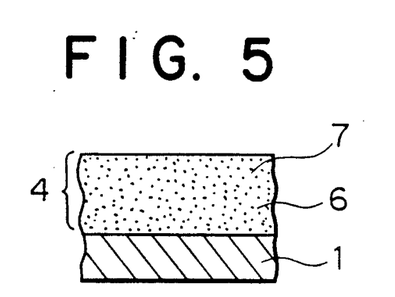
Figure 6:
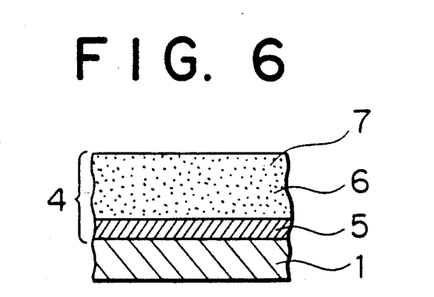

As shown in FIGS. 3 or 4, the photosensitive layer 4 may also be provided interposing an intermediate layer 5 provided on the conductive support. A photoreceptor having best electrophotographic characteristics can be obtained when the photosensitive layer 4 is thus comprised of the two layers. In the present invention, as shown in FIGS. 5 or 6, a photosensitive layer 4 comprising the carrier-generating material 7 dispersed in a layer 6 mainly composed of a carrier-transporting material may be provided on a conductive support 1 directly or interposing an intermediate layer 5. In the present invention, a protective layer 8 may also be provided as an outermost layer, as shown in FIG. 4.

In the photoreceptor, the compound represented by Formula I of the present invention is added as the carrier-transporting material.

The carrier-generating material used in the carrier generation layer of the photosensitive layer according to the present invention includes the following:

(1) Azo dyes such as a monoazo dye, a disazo dye and a trisazo dye.
(2) Perylene dyes such as perylenic anhydride and perylenic acid imide.
(3) Indigo dyes such as indigo and thioindigo.
(4) Polycyclic quinones such as anthraquinone, pyrenequinone and flavanthrones.
(5) Quinacridone dyes.
(6) Bisbenzoimidazole dyes.
(7) Indanthrone dyes.
(8) Squalirium dyes.
(9) Cyanine dyes.
(10) Azulenium dyes.
(11) Triphenylmethane dyes.
(12) Amorphous silicon.
(13) Phthalocyanine dyes such as a metallic phthalocyanine and a non-metallic phthalocyanine.
(14) Selenium, selenium-tellurium, and selenium-arsenic.
(15) CdS, and CaSe.
(16) Pyrylium salt dyes, and thiapyrylium dyes.

These can be used alone or in the form of a mixture of two or more kinds.

The compound of Formula I according to the present invention and most of the carrier-generating material have no film forming properties in itself, and hence various binders are used in combination to form the photosensitive layer.

Any binders can be used here, but it is preferred to use a high polymer which is hydrophobic, has a high dielectric constant, and is capable of forming an electrically insulating film. Such a high polymer includes the following, but is by no means limited to these:
(P-1) Polycarbonate
(P-2) Polyester
(P-3) Methacrylic resin
(P-4) Acrylic resin
(P-5) Polyvinyl chloride
(P-6) Polyvinylidene chloride
(P-7) Polystyrene
(P-8) Polyvinyl acetate
(P-9) Styrene/butadiene copolymer
(P-10) Vinylidene chloride/acrylonitrile copolymer
(P-11) Vinyl chloride/vinyl acetate copolymer
(P-12) Vinyl chloride/vinyl acetate/maleic anhydride copolymer
(P-13) Silicone resin
(P-14) Silicone-alkyd resin
(P-15) Phenol-formaldehyde resin
(P-16) Styrene-alkyd resin
(P-17) Poly-N-vinylcarbazole
(P-18) Polyvinylbutyral
(P-19) Polyvinylformal These binder resins can be used alone or in the form of a mixture of two or more kinds.

A solvent used for the formation of the carrier generation layer and the carrier transport layer according to the present invention includes N,N-dimethylformamide, acetone, methyl ethyl ketone, cyclohexanone, benzene, toluene, xylene, chloroform, 1,2-dichloroethane, 1,2-dichloropropane, 1,1,2-trichloroethane, 1,1,1-trichloroethane, trichloroethylene, tetrachloroethane, dichloromethane, tetrahydrofuran, dioxane, methanol, ethanol, isopropanol, ethyl acetate, butyl acetate, dimethyl sulfoxide, and methyl cellosolve, which can be used by mixture.

In the case when the photoreceptor of the present invention has a laminated structure, the carrier generation layer may contain the carrier-transporting material together with the carrier-generating material. The weight ratio of the binder : carrier-generating material : carrier-transporting material in the carrier generation layer may preferably be 0 to 100 : 1 to 500 : 0 to 500.

If the carrier-generating material is contained in an amount less than the above, a low photosensitivity may result to cause an increase in residual potential. On the other hand, if it is contained in an amount more than the above, the dark decay and receptive potential may be lowered.

The carrier-transporting material represented by Formula I of the present invention may preferably be used in an amount of from 20 to 200 parts by weight, and particularly preferably from 30 to 150 parts by weight, based on 100 parts by weight of the binder resin contained in the carrier transport layer.

The carrier generation layer thus formed may preferably have a coating thickness of from 0.01 to 10 $\mu$m, and particularly preferably from 0.1 to 5 $\mu$m.

The carrier transport layer also formed may preferably have a coating thickness of from 5 to 50 $\mu$m, and particularly preferably from 5 to 30 $\mu$m.

On the other hand, when the photoreceptor of the present invention is comprised of a single-layer function-separated type, the weight ratio of the binder : carrier-generating material : carrier-transporting material of the present invention in the photosensitive layer may preferably be 0 to 100 : 1 to 500 : 0 to 500. The photosensitive layer thus formed may preferably have a coating thickness of from 5 to 50 $\mu$m, and particularly preferably from 5 to 30 $\mu$m.

The conductive support used in the electrophotographic photoreceptor of the present invention includes a sheet or drum made of a metal including an alloy, or a paper or plastic film made conductive by the coating, deposition or lamination of a thin film of a conductive compound such as a conductive polymer or indium oxide or a thin film of a metal such as aluminum, palladium or gold including an alloy thereof.

As a binder used in an intermediate layer and a protective layer, the binder used for the above carrier generation layer and carrier transport layer can be used. In addition thereto, also effective are polyamide resins, nylon resins, ethylene resins such as an ethylene/vinyl acetate copolymer, an ethylene/vinyl acetate/maleic anhydride copolymer and an ethylene/vinyl acetate/methacrylic acid copolymer, polyvinyl alcohol, and cellulose derivatives.

An organic amine can be added to the photosensitive layer of the present invention for the purpose of improving a carrier-generating function of the carrier-generating material. Among organic amines, it is particularly preferred to add a secondary amine.

The above photosensitive layer may also contain anti-deterioration agents such as an antioxidant or a light stabilizer for the purpose of improving storage stability, durability and resistance to environmental condition. Effective compounds used for such purpose include, for example, chromanol derivatives such as tocopherol, and etherified compounds or esterified compounds thereof, polyarylalkane compounds, hydroquinone derivatives and mono- or dietherified compounds thereof, benzophenone derivatives, benzotriazole derivatives, thioether compounds, phosphonic acid esters, phosphorous acid esters, phenylenediamine derivatives, phenol compounds, hindered phenol compounds, straight-chain amine compounds, cyclic amine compounds, and hindered amine compounds. Examples of particularly effective compounds are hindered phenol compounds such as IRGANOX 1010, IRGANOX 565 (products of Ciba-Geigy Corp.), Sumilizer BHT, and Sumilizer MDP (products of Sumitomo Chemical Co., Ltd.), and hindered amine compounds such as SANOL LS-2626 and SANOL LS-622LD.

In the present invention, the carrier generation layer may be incorporated with one or more kinds of an electron acceptive substance for the purposes of improving sensitivity and decreasing the residual potential or the fatigue in repeated use.

The electron acceptive substance that can used here includes, for example, succinic anhydride, maleic anhydride, dibromomaleic anhydride, phthalic anhydride, tetrachlorophthalic anhydride, tetrabromophthalic anhydride, 3-nitrophthalic anhydride, 4-nitrophthalic anhydride, pyromellitic anhydride, mellitic anhydride, tetracyano ethylene, tetracyanoquinodimethane, o-dinitrobenzene, m-dinitrobenzene, 1,3,5-trinitrobenzene, paranitrobenzonitrile, picryl chloride, quinonechloroimide, chloranil, bromanil, dichlorodicyanoparabenzoquinone, anthraquinone, dinitroanthraquinone, 2,7-dinitrofluolenone, 2,4,7-trinitrofluolenone, 2,4,5,7-tetranitrofluolenone, 9-fluolenylidene-malonodinitrile, polynitro-9-fluolenylidenemalonodinitrile, picric acid, o-nitrobenzoic acid, p-nitrobenzoic acid, 3,5-dinitrobenzoic acid, pentafluorobenzoic acid, 5-nitrosalicylic acid, 3,5-dinitrosalicylic acid, phthalic acid, mellitic acid, an other compounds having a large electron affinity.

The electron acceptive substance may be added in an amount of 100:0.01 to 200, and preferably 100:0.1 to 100, in terms of weight ratio of carrier-generating material to electron acceptive substance.

The electron acceptive substance may also be added to the carrier transport layer. When the electron acceptive substance is added to such a layer, it may be added in an amount of 100:0.01 to 100, and preferably 100:0.1 to 50, in terms of weight ratio of carrier-transporting material to electron acceptive substance.

In addition to the above, the photoreceptor of the present invention may also optionally contain an ultraviolet absorbent or the like for the purpose of protecting the photosensitive layer, or may also contain a dye for correcting color sensitivity.

The electrophotographic photoreceptor of the present invention has the constitution as described above. As will be also evident from Examples described below, it has superior charge characteristics, sensitivity characteristics and image formation characteristics. In particular, it causes less fatigue deterioration even after repeated use, thus having a superior durability.

The electrophotographic photoreceptor of the present invention can be widely used not only in electrophotographic copying machines but also in the field in which electrophotography is applied, as in a photoreceptor of a printer using a laser, a cathode ray tube (CRT) or a light-emitting diode (LED) as a light source.

EXAMPLES

Example 1

On a conductive support comprising a polyester film on which aluminum was deposited, an intermediate layer of 0.04 μm in thickness, comprising a vinyl chloride/vinyl acetate/maleic anhydride copolymer (S-LEC MF-10, a product of Sekisui Chemical Co., Ltd., was provided. A coating solution was prepared by dissolving and thoroughly mixing 1.5 g of polycarbonate, Panlite L-1250 (a product of Teijin Chemicals Ltd.), in a dispersion obtained by dispersing 1 g of dibromoanthanthrone, Monolite Red 2Y (C.I. No. 59300, a product of ICI Inc.), in 30 ml of 1,2-dichloroethene by means of a ball mill. The resulting coating solution was coated on the above intermediate layer in a dry coating thickness of 2 μm to form a carrier generation layer.

On the layer thus formed, a solution obtained by dissolving 5 g of Exemplary Compound 14 and 10 g of polycarbonate, Z-200 (a product of Mitsubishi Gas Chemical Company, Inc.), in 80 ml of 1,2-dichloroethane was coated in a dry coating thickness of 20 μm to form a carrier transport layer. A photoreceptor of the present invention was thus prepared.

In respect of the photoreceptor thus obtained, the following characteristics were evaluated using EPA-8100, manufactured by Kawaguchi Denki K. K. The photoreceptor was charged for 5 seconds at a charge voltage of −6 kV, and thereafter left to stand for 5 seconds, followed by irradiation with light from a halogen lamp so as to give an illumination of 2 lux at the surface of the photoreceptor, where initial surface potential $V_A$ and half decay exposure $E_{\frac{1}{2}}$ were determined. Residual potential $V_R$ was also determined after the photoreceptor was exposed to light at an exposure of 30 lux.sec. Similar measurement was repeated 1,000 times. Results obtained are shown in Table 1.

TABLE 1

|  | Initial stage | | | After 1,000 times | | |
|---|---|---|---|---|---|---|
|  | (V) $-V_A$ | (lux · sec) $E_{\frac{1}{2}}$ | (V) $-V_R$ | (V) $-V_A$ | (lux · sec) $E_{\frac{1}{2}}$ | (V) $-V_R$ |
| Example 1: | 1,130 | 2.1 | 0 | 1,125 | 2.2 | 0 |

Examples 2 to 10

Photoreceptors were prepared and similar measurement was made in the same manner as in Example 1 except that Exemplary Compound 14 was replaced with the exemplary compounds as shown in the following Table 2.

TABLE 2

| Example | Exemplary compound | Initial stage | | | After 1,000 times | | |
|---|---|---|---|---|---|---|---|
|  |  | (V) $-V_A$ | (lux · sec) $E_{\frac{1}{2}}$ | (V) $-V_R$ | (V) $-V_A$ | (lux · sec) $E_{\frac{1}{2}}$ | (V) $-V_R$ |
| 2 | 1 | 1,200 | 2.6 | 0 | 1,180 | 2.7 | 0 |
| 3 | 4 | 1,090 | 2.5 | 0 | 1,085 | 2.6 | 0 |
| 4 | 15 | 1,070 | 2.2 | 0 | 1,060 | 2.3 | 0 |
| 5 | 16 | 1,120 | 2.1 | 0 | 1,100 | 2.2 | 0 |
| 6 | 27 | 1,210 | 2.4 | 0 | 1,210 | 2.5 | 0 |
| 7 | 28 | 1,080 | 2.4 | 0 | 1,055 | 2.5 | 0 |
| 8 | 40 | 1,010 | 2.1 | 0 | 1,000 | 2.2 | 0 |
| 9 | 41 | 1,100 | 2.2 | 0 | 1,090 | 2.3 | 0 |
| 10 | 53 | 1,130 | 2.1 | 0 | 1,120 | 2.2 | 0 |

Comparative Example 1

A comparative photoreceptor was prepared in the same manner as in Example 1 except for using the following compound as a carrier-transporting material.

On this comparative photoreceptor, measurement was made in the same manner as in Example 1 to obtain the results shown in Table 3.

TABLE 3

|  | Initial stage | | | After 1,000 times | | |
|---|---|---|---|---|---|---|
|  | (V) $-V_A$ | (lux · sec) $E_{\frac{1}{2}}$ | (V) $-V_R$ | (V) $-V_A$ | (lux · sec) $E_{\frac{1}{2}}$ | (V) $-V_R$ |
| Comparative Example 1: | 980 | 3.9 | 0 | 910 | 4.1 | 15 |

Example 11

On a conductive support comprising a polyester film on which aluminum was deposited, an intermediate layer of 0.1 μm in thickness, comprising a polyamide resin A-70, a product of Toray Industries, Ltd., was provided.

In 100 ml of 1,2-dichloroethane, 2 g of a bisazo pigment having the above structure and 2 g of a polycarbonate resin, Panlite L-1250 (a product of Teijin Chemicals Ltd.), were mixed, and then dispersed for 8 hours using a sand grinder. The resulting dispersion was coated on the intermediate layer in a dry coating thickness of 0.2 μm.

Using Exemplary Compound 3 as a carrier-transporting material and with addition of an anti-deterioration agent IRGANOX 1010 in an amount of 1.5 wt. % based on the carrier-transporting material, a photoreceptor was prepared in the same manner as in Example 1. On this photoreceptor, measurement was also made in the same manner as in Example 1 to obtain the results shown in Table 4.

TABLE 4

|  | Initial stage | | | After 1,000 times | | |
|---|---|---|---|---|---|---|
|  | (V) $-V_A$ | (lux · sec) $E_{\frac{1}{2}}$ | (V) $-V_R$ | (V) $-V_A$ | (lux · sec) $E_{\frac{1}{2}}$ | (V) $-V_R$ |
| Example 11: | 1,410 | 0.8 | 0 | 1,400 | 0.9 | 0 |

Examples 12 to 20

Photoreceptors were prepared and measurement was made in the same manner as in Example 1 except that Exemplary Compound 3 was replaced with the exemplary compounds as shown in the following Table 5.

TABLE 5

| Example | Exemplary compound | Initial stage | | | After 1,000 times | | |
|---|---|---|---|---|---|---|---|
|  |  | (V) $-V_A$ | (lux · sec) $E_{\frac{1}{2}}$ | (V) $-V_R$ | (V) $-V_A$ | (lux · sec) $E_{\frac{1}{2}}$ | (V) $-V_R$ |
| 12 | 1 | 1,400 | 1.2 | 0 | 1,380 | 1.3 | 0 |
| 13 | 4 | 1,370 | 1.1 | 0 | 1,360 | 1.2 | 0 |
| 14 | 15 | 1,320 | 0.9 | 0 | 1,310 | 0.9 | 0 |
| 15 | 16 | 1,350 | 0.9 | 0 | 1,340 | 1.0 | 0 |
| 16 | 27 | 1,410 | 1.0 | 0 | 1,400 | 1.1 | 0 |
| 17 | 28 | 1,380 | 1.1 | 0 | 1,370 | 1.2 | 0 |
| 18 | 40 | 1,410 | 0.8 | 0 | 1,390 | 0.9 | 0 |
| 19 | 41 | 1,390 | 0.9 | 0 | 1,370 | 1.0 | 0 |
| 20 | 53 | 1,400 | 0.8 | 0 | 1,380 | 1.0 | 0 |

Comparative Examples 2 and 3

Comparative photoreceptors were prepared in the same manner as in Example 11 except for using the following compounds, respectively, as a carrier-transporting material.

On the resulting comparative photoreceptors, measurement was made in the same manner as in Example 1 to obtain the results shown in Table 6.

TABLE 6

| Comparative Example: | Initial stage | | | After 1,000 times | | |
|---|---|---|---|---|---|---|
|  | (V) $-V_a$ | (lux · sec) $E_{\frac{1}{2}}$ | (V) $-V_R$ | (V) $-V_A$ | (lux · sec) $E_{\frac{1}{2}}$ | (V) $-V_R$ |
| 2 | 910 | 2.6 | 0 | 830 | 2.9 | 23 |
| 3 | 1,160 | 1.6 | 0 | 1,007 | 1.9 | 18 |

Comparative Example 4

A comparative photoreceptor was prepared in the same manner as in Example 11 except for using the following compound as a carrier-transporting material.

In respect of the resulting photoreceptor and the photoreceptor of Example 11, the amount of light necessary for decaying the surface potential from 300 V to 20 V was determined. Results are shown below.

|  | $E_{20}^{300}$ Initial stage | lux · sec After 1,000 times |
| --- | --- | --- |
| Example 11: | 0.9 | 1.0 |
| Comparative Example 4: | 1.1 | 1.3 |

Example 21

A solution obtained by dissolving 1 g of Exemplary Compound 1 as the carrier-transporting material of the present invention and 1.5 g of a polyester resin Byron 200 (a product of Toyobo Co., Ltd.) in 10 g of 1,2-dichloroethane was coated on an aluminum drum by dip coating, followed by drying to form a carrier transport layer with a coating thickness of 15 μm. On the other hand, 1 g of titanylphthalocyanine having major peaks in terms of Bragg's $2\theta$ angle to CuKα characteristic X-ray wavelength at 1.541 Å at least at 9.5±0.2 degrees, 11.7±0.2 degrees, 15.0±0.2 degrees, 23.5±0.2 degrees, 24.1±0.2 degrees and 27.3±0.2 degrees, which is disclosed in Japanese Patent O.P.I. Publication No. 17065/1989, as a carrier-generating material, 3 g of polycarbonate Panlite L-1250 (a product of Teijin chemicals Ltd.) as a binder resin, 15 g of monochlorobenzene as a dispersion medium and 35 g of 1,2-dichloroethane were dispersed using a ball mill. Thereafter, Exemplary Compound 1 as a carrier-transporting material was added in an amount of 74 wt. % based on the binder resin. A dispersion thus obtained was coated on the above carrier transport layer by spray coating to form a carrier generation layer with a coating thickness of 2 μm.

The photoreceptor thus prepared was evaluated in the same manner as the evaluation in Example 1 except that the charge polarity was made positive.

The following results were obtained.

$V_a = 1,510$ (V)

$E_{\frac{1}{2}} = 0.8$ (lux.sec)

Example 22

On an aluminum drum, an intermediate layer of 0.15 μm in thickness, comprising a vinyl chloride/vinyl acetate/maleic anhydride copolymer (S-LEC MF-10, a product of Sekisui Chemical Co., Ltd.) was formed. On the other hand, 1 g of dibromoanthanthrone Monolite Red 2Y as a carrier-generating material was pulverized in a ball mill, and a solution comprising 3 g of a polycarbonate resin Panlite L-1250, 15 g of monochlorobenzene and 35 g of 1,2-dichloroethane was added and then dispersed. To the resulting dispersion, 2 g of a carrier-transporting material of the present invention, Exemplary Compound 1, was further added, and the solution thus obtained was coated on the above intermediate layer by spray coating, followed by drying to form a photosensitive layer with a thickness of 20 μm.

The photoreceptor thus prepared was evaluated in the same manner as the evaluation in Example 1 except that the charge polarity was made positive, and the following results were obtained.

$V_a = 1,121$ (V)

$E_{\frac{1}{2}} = 2.8$ (lux.sec)

What is claimed is:

1. An electrophotographic photoreceptor comprising:

a conductive support, and having provided thereon a photosensitive layer comprising a carrier-generation layer comprising a carrier-generating substance and a carrier-transport layer comprising a compound represented by Formula I:

(I)

wherein Ar is a substituted or unsubstituted arylene group; $R_1$ and $R_2$ are each a substituted or unsubstituted aryl group; $R_3$ and $R_4$ are each a hydrogen atom, a hydroxyl group, a substituted or unsubstituted alkoxy group having 1 to 5 carbon atoms or a substituted or unsubstituted alkyl group having 1 to 5 carbon atoms.

2. The photoreceptor of claim 1, wherein said carrier-transport layer comprises a binder resin and said compound represented by Formula I and the content of said compound represented by Formula I is 20 to 200 parts per 100 parts by weight of said binder resin.

3. The photoreceptor of claim 2, wherein the content of said compound represented by Formula I is 30 to 150 parts per 100 parts by weight of said binder resin.

* * * * *